United States Patent
Lesur et al.

[11] Patent Number: 5,998,448
[45] Date of Patent: *Dec. 7, 1999

[54] COMBINED PREPARATIONS WITH VASCULAR EFFECT CONTAINING DIHYDROPYRIDINES ACETYLSALICYLIC ACID NITROESTERS AND VITAMINS

[75] Inventors: Eva Lesur, Köln; Dieter Neuser, Langenfeld; Oswald Lockhoff, Leverkusen; Elisabeth Perzborn, Wuppertal; Johannes Peter Stasch, Solingen; Peter Kurka, Langenfeld, all of Germany

[73] Assignee: Bayer Aktiengeselechaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/945,516
[22] PCT Filed: Apr. 19, 1996
[86] PCT No.: PCT/EP96/01631
  § 371 Date: Oct. 24, 1997
  § 102(e) Date: Oct. 24, 1997
[87] PCT Pub. No.: WO96/34607
  PCT Pub. Date: Nov. 7, 1996

[30] Foreign Application Priority Data

May 2, 1995 [DE] Germany .............. 195 15 971

[51] Int. Cl.[6] ............ C07D 211/80; A61K 31/435
[52] U.S. Cl. .............. 514/344; 514/356; 546/286; 546/321
[58] Field of Search .............. 546/286, 321; 514/344, 556

[56] References Cited

PUBLICATIONS

Dong et al., Chin. J. Cariol. 18 (5), 301 (1990).
Dobrotvorskaya et al., Klin.Med. (Mosk.) 67 (II) (1993) (English Summary appears on page 43 of the reference.).
Coma–Canella et al., Am.Heart.J. 124 (5), 1196 (1992).
Nunes et al., RIC SCI Suppl. 90, Abstract 526 (1991).
Kovacs et al., Throm.Haemost 69 (6), 634 (1993).
Darius et al., Z. Kardiol. 80 (Suppl. 5) (1991) (English Summary appears on page 47 of this reference.).
Tison et al., Am.J.Hypertension, 46S–49S (1994).
Fetkovska et al., Am.J.Hypertension, 98S–101S (1993).
Tison et al., Blood Pres.Suppl., 57–60 (1994).
Folts et al., Med.Sci.Symp.Ser., 165–71 (1993).
English Abstract of Dong et al., Chin J. Cariol. 18 (5), 301 (1990).

*Primary Examiner*—Zinna Northington Davis
*Attorney, Agent, or Firm*—Sprung Kramer Schaefer & Briscoe

[57] ABSTRACT

The invention relates to new combinations of dihydropyridines of the general formula (I)

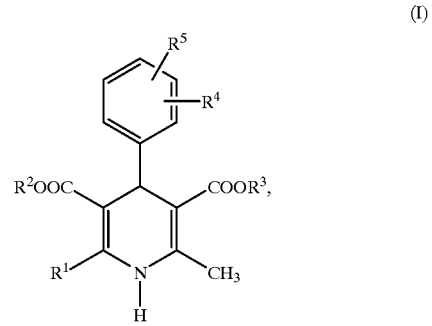

in which $R^1$ to $R^5$ have the meaning indicated in the description, for the prevention and treatment of vascular disorders, in particular of cardiovascular and cerebrovascular disorders, containing dihydropyridines having calcium antagonist activity, acetylsalicylic acid nitroesters and vitamins, and, if appropriate, also further auxiliaries or active compounds.

5 Claims, No Drawings

COMBINED PREPARATIONS WITH VASCULAR EFFECT CONTAINING DIHYDROPYRIDINES ACETYLSALICYLIC ACID NITROESTERS AND VITAMINS

This application is a 371 of PCT/EP96/01631 filed Apr. 19, 1996.

The invention relates to novel combination preparations for the prevention and treatment of vascular disorders, in particular of cardiovascular and cerebrovascular disorders, containing dihydropyridines which have calcium antagonist activity, acetylsalicylic acid nitroesters and vitamins, and, if appropriate, also further auxiliaries or active compounds.

The individual elements of the combination according to the invention and its therapeutic actions on the vascular system are well known. This applies in particular to the calcium antagonist active compounds and to acetylsalicylic acid, subsequently called ASA, and some of its derivatives. It is furthermore known that, for example, ASA or calcium antagonist dihydropyridines such as nifedipine and also combinations of these active compounds possess a positive synergistic effect on thrombogenesis (cf. E. Dong et al., Effects of the combination of Aspirin and Nifedipine on platelet aggregation and thrombogenesis, Chin. J. Cardiol. 18 (5), 301 (1990)). It was not possible however, to achieve a reduction of already present lesions using dihydropyridines.

Combinations of parenterally administered nitroglycerin with nifedipine, isosorbide dinaitrate, heparin and ASA show a clearly antiarrhythmic effect on unstable angina pectoris at the end of the first week of treatment, which also persists on further treatment with a lower dose (cf. T. E. Dobrotvorskaya et al., Antiarrhythmic effect of Cordaron in patients with unstable angina pectoris and myocardial infarction, Klin. Med. (Mosk.) 67 (II) (1993)).

The positive synergistic actions of ASA in combination with nifedipine were tested and confirmed in numerous clinical investigations (cf. I. Coma-Canella, Detection of restenosis with dobutamine stress after coronary angioplasty, Am. Heart J. 124 (5), 1196 (1992)); J. P. Nunes et al., The effect of low dose Aspirin on blood pressure in treated hypertensive patients, RIC SCI (Suppl. 90), Abstract 526 (1991); I. B. Kovacs, Addition of Nifedipine to Aspirin improves platelet reactivity in cardiac patients who fail to respond to Aspirin alone, Thromb. Haemost, 69 (6), 634 (1993); H. Darius et al., Beeinflussung der Thrombozytenfunktion bei diagnostischen und therapeutischen Eingriffen in der Cardiologie [Effect of platelet function on diagnostic and therapeutic interventions in cardiology], 80 (Suppl. 5), (1991)).

ASA is only employed for the prophylaxis of thromboembolic and cardiovascular events. ASA derivatives which are cleaved in vivo into ASA and nitrogen oxides are also known and should have fewer gastrointestinal side effects with the same potency of action as ASA (cf. WO 92/01668, 6.2.1992).

The positive effects of vegetable gingko preparations and of vitamins, in particular of vitamins A, B, C and E, are also known from numerous publications.

The invention relates to new combinations of dihydropyridines of the general formula (I)

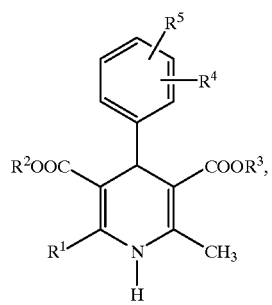

in which
R$^1$ represents cyano or alkyl having 1 to 4 C atoms, which is optionally substituted by hydroxyl, or the radical OCH$_2$CH$_2$NH$_2$,
R$^2$ and R$^3$ are identical or different and in each case represent alkyl having 1 to 4 C atoms, which is optionally substituted by alkoxy having 1 to 4 C atoms or by an N-methylbenzyl radical,
R$^4$ and R$^5$ are identical or different and in each case represent hydrogen, nitro, trifluoromethyl, chlorine or the radical OCHF$_2$ or together with the phenyl, ring represent the radical

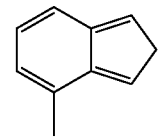

with acetylsalicylic acid nitroesters of the formula (II)

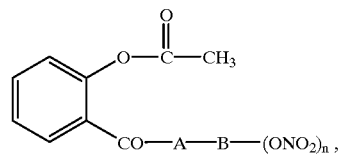

in which
A represents oxygen or NH,
B represents a straight-chain or branched alkylene radical having 2 to 7 C atoms, a cycloalkylene radical having 3 to 7 C atoms or an aralkylene radical having 7 to 12 C atoms and
n represents a number from 1 to 5, preferably 1 to 3, and with at least one vitamin from the group consisting of the vitamins A, B, C, D, E and β-carotene, and, if appropriate, gingko extract as a further active compound component.

Active compounds of interest from the dihydropyridines class which may be mentioned are nifedipine, amlodipine, nimodipine, nitrendipine and nisoldipine.

For the treatment of cerebrovascular disorders, combination therapy with nimodipine is particularly to be recommended. For treatment of cardiovascular disorders, combinations which contain nifedipine or amlodipine are of particular interest.

Those combinations according to the invention are of particular interest which contain ASA derivatives of the formula (II) in which A represents oxygen and B represents an alkylene group having 2 to 6 carbon atoms and n represents a number from 1 to 3.

These ASA derivatives are distinguished by particularly good tolerability and are therefore suitable for the prophylaxis and continuous therapy of appropriate vascular disorders.

Surprisingly, it appears that the new combination of at least three known active compound types, the dihydropyridines, the ASA derivatives and the vitamins, and, if appropriate, the further addition of gingko extracts represent a particularly effective and highly tolerable means for the treatment of cerebrovascular and cardiovascular disorders. The positive properties of these new combinations result from the superadditive effects of the individual combination components.

The combination according to the invention can be employed in customary administration forms for oral administration. The following may preferably be mentioned: tablets, pills, coated tablets, capsules, solutions, drops and sprays.

WORKING EXAMPLES

Example 1

Rapid-Release Effervescent Tablet

| | |
|---|---|
| ASA | 100 mg |
| Nifedipine | 10 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 2740 mg |

Preparation:

Sodium citrate, citric acid, ascorbic acid, nifedipine and nicotinamide are granulated with water in a fluidized bed and then dried. The grain size of the granules is preferably 90% between 125 and 400 µm.

The remaining constituents (acetylsalicylic acid, vitamin A, riboflavin, pyridoxine HCl, cyanocobalamin, D-α-tocopherol acetate, dry extract of Gingko biloba leaves) are admixed to these granules under suitable climatic conditions and this mixture is compressed in suitable tablet presses to give effervescent tablets having a diameter of 20 mm. The tablets are then packed, e.g. in aluminium/aluminium blister packs.

Examples 2 to 6 and 12 to 14 are prepared analogously.

Example 2

Rapid-Release Effervescent Tablet

| | |
|---|---|
| ASA | 500 mg |
| Nifedipine | 90 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3220 mg |

Example 3

Rapid-Release Effervescent Tablet

| | |
|---|---|
| NO-ASA | 500 mg |
| Nifedipine | 90 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3220 mg |

| | |
|---|---|
| NO-ASA | 500 mg |
| Amlodipine | 90 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3220 mg |

Example 5

Rapid-Release Effervescent Tablet

| | |
|---|---|
| ASA | 500 mg |
| Amlodipine | 90 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3220 mg |

Example 6

Rapid-Release Effervescent Tablet

| | |
|---|---|
| ASA | 100 mg |
| Amlodipine | 10 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 2740 mg |

Example 7

Delayed-Release Tablet

| | |
|---|---|
| ASA | 100 mg |
| Amlodipine | 30 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Metholose 60 SH 50 | 400 mg |
| Mg stearate | 4 mg |
| Total weight | 915 mg |

Preparation

All substances used with the exception of magnesium stearate are homogeneously mixed in suitable mixers and then dry-compacted on suitable rolls. The shells resulting in this process are broken in the compactor with the aid of a suitable sieve to give granules having a grain size distribution of preferably between 63 and 400 µm.

The granules are then mixed with magnesium stearate and compressed to give oblong tablets. The tablets are then packed, e.g. in aluminium/aluminium blister packs.

Examples 8 to 10 are prepared analogously.

Example 8

Delayed Release Tablet

| | |
|---|---|
| ASA | 100 mg |
| Nifedipine | 30 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Metholose 60 SH 50 | 400 mg |
| Mg stearate | 4 mg |
| Total weight | 915 mg |

Example 9

Delayed Release Tablet

| | |
|---|---|
| NO-ASA | 100 mg |
| Nifedipine | 30 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Metholose 60 SH 50 | 400 mg |
| Mg stearate | 4 mg |
| Total weight | 915 mg |

Example 10

Delayed Release Tablet

| | |
|---|---|
| NO-ASA | 100 mg |
| Amlodipine | 30 mg |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-αtocopherol acetate | 15 mg |
| Dry extract of Gingko biloba leaves (50:1) standardized to 960 mg of gingko flavone glycosides and 240 mg of terpene lactones | 40 mg |
| Metholose 60 SH 50 | 400 mg |
| Mg stearate | 4 mg |
| Total weight | 915 mg |

For the following examples, a coprecipitate is employed on the grounds of the low solubility of nimodipine. This coprecipitate releases nimodipine rapidly and in supersaturated form in vitro, so that the active compound is rapidly bioavailable in vivo.

Composition of the coprecipitate:

| | |
|---|---|
| Nimodipine | 1 part |
| PVP | 3 parts |
| Acetone or ethanol | q.s. |

Preparation of the coprecipitate:

Nimodipine and PVP are dissolved in an adequate amount of acetone or ethanol. The solvent is then stripped off with heating and under reduced pressure and the resulting nimodipine/PVP coprecipitate is dried at elevated temperature (>90° C.) until the residual content of solvent is less than 200 ppm. The nimodipine coprecipitate prepared in this way is amorphous to X-ray and releases nimodipine rapidly and in supersaturated form. The coprecipitate is ground and classified in suitable apparatuses. The ratio between nimodipine and PVP can be varied between 1:1 and 1:5.

Example 11

Rapid Release Effervescent Tablet

| | |
|---|---|
| ASA | 100 mg |
| Nimodipine coprecipitate | 40 mg (10 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 2770 mg |

Example 12

Rapid Release Effervescent Tablet

| | |
|---|---|
| ASA | 500 mg |
| Nimodipine coprecipitate | 120 mg (30 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3250 mg |

Example 13

Rapid Release Effervescent Tablet

| | |
|---|---|
| NO-ASA | 500 mg |
| Nimodipine coprecipitate | 360 mg (90 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 3490 mg |

Example 14

Effervescent Tablet

| | |
|---|---|
| NO-ASA | 100 mg |
| Nimodipine coprecipitate | 40 mg (10 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 100 mg |
| Ascorbic acid | 200 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Sodium citrate, primary | 1306 mg |
| Citric acid, powder | 260 mg |
| Sodium hydrogen carbonate | 483 mg |
| Sodium carbonate | 200 mg |
| Total weight | 2770 mg |

Example 15

Rapid Release Tablet

| | |
|---|---|
| NO-ASA | 100 mg |
| Nimodipine coprecipitate | 120 mg (30 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 50 mg |
| Ascorbic acid | 50 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Maize starch | 150 mg |
| Avicel | 50 mg |
| Polyplasdone XL | 20 mg |
| Magnesium stearate | 3 mg |
| Total weight | 624 mg |

Preparation

Maize starch, Avicel, Polyplasdone, ascorbic acid, nicotinamide, riboflavin and thiamine nitrate, pyridoxine HCl are granulated with water in a fluidized bed and then dried. The grain size of the granules is preferably to 90% between 125 and 400 µm.

NO-ASA, the nimodipine coprecipitate, vitamin A, pyridoxine HCl, cyano-cobalamin, D-α-tocopherol acetate, the dry extract of Gingko biloba leaves and magnesium stearate are admixed to these granules and the mixture is compressed in suitable tablet presses to give oblong tablets.

Example 16

Rapid Release Tablet

| | |
|---|---|
| NO-ASA | 30 mg |
| Nimodipine coprecipitate | 40 mg (10 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 50 mg |
| Ascorbic acid | 50 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| Maize starch | 150 mg |
| Avicel | 50 mg |
| Polyplasdone XL | 20 mg |
| Magnesium stearate | 3 mg |
| Total weight | 474 mg |

Preparation

All constituents with the exception of the nimodipine coprecipitate, the NO-ASA and the magnesium stearate are moistened with a suitable amount of water in a customary mixer. This mixture is consolidated in an extruder under suitable conditions and, for example, extruded through a 1 mm sieve plate. If required, the extrudate strips thus obtained are rounded off in a spheronizer and then dried.

The dried extrudate is mixed with the nimodipine coprecipitate, NO-ASA and magnesium stearate and compressed in suitable tablet machines ( 11 mm diameter).

Example 17

Rapid Release Tablet

| | |
|---|---|
| NO-ASA | 30 mg |
| Nimodipine coprecipitate | 40 mg (10 mg nimodipine) |
| Dry extract of Gingko biloba leaves (50:1) standardized to 960 mg of gingko flavone glycosides and 240 mg of terpene lactones | 40 mg |
| Maize starch | 100 mg |
| Avicel | 50 mg |
| Polyplasdone XL | 10 mg |
| Magnesium stearate | 3 mg |
| Total weight | 273 mg |

Preparation

The gingko dry extract is moistened with maize starch, Avicel and Polyplasdone in a customary mixer using an adequate amount of water. This mixture is consolidated under suitable conditions in an extruder and, for example, extruded through a 1 mm sieve plate. If required, the extrudate strips thus obtained are rounded off in a spheronizer and then dried.

The dried extrudate is mixed with the nimodipine coprecipitate, NO-ASA and magnesium stearate and compressed in suitable tablet machines (9 mm diameter).

Example 18

Rapid Release Tablet

| | |
|---|---|
| NO-ASA | 100 mg |
| Nimodipine coprecipitate | 120 mg (30 mg nimodipine) |
| Dry extract of Gingko biloba leaves (50:1) standardized to 960 mg of gingko flavone glycosides and 240 mg of terpene lactones | 40 mg |
| Maize starch | 150 mg |
| Avicel | 80 mg |
| Polyplasdone XL | 10 mg |
| Magnesium stearate | 3 mg |
| Total weight | 503 mg |

Preparation

The gingko dry extract is moistened with maize starch, Avicel and Polyplasdone in a customary mixer using an adequate amount of water. This mixture is consolidated under suitable conditions in an extruder and, for example, extruded through a 1 mm sieve plate. If required, the extrudate strips thus obtained are rounded off in a spheronizer and then dried.

The dried extrudate is mixed with the nimodipine coprecipitate, NO-ASA and magnesium stearate and compressed in suitable tablet machines (11 mm diameter).

Example 19

Delayed Release Tablet

For delayed release tablets, a special nimodipine coprecipitate must be prepared which allows a supersaturated release over several hours.

Composition of the coprecipitate

| | |
|---|---|
| Nimodipine | 22.2% |
| PVP K 25 | 55.6% |
| Crospovidone M | 22.2% |
| Acetone | q.s. |

The preparation of this delayed release coprecipitate is carried out analogously to the process in Working Example 11.

| | |
|---|---|
| NO-ASA | 100 mg |
| Nimodipine coprecipitate | 120 mg (30 mg nimodipine) |
| Dry extract of Gingko biloba leaves (50:1) standardized to 960 mg of gingko flavone glycosides and 240 mg of terpene lactones | 40 mg |
| HPMC 60 SH 50 | 200 mg |
| Magnesium stearate | 3 mg |
| Total weight | 463 mg |

Preparation

The gingko dry extract is moistened with maize starch, Avicel and Polyplasdone in a customary mixer using an adequate amount of water. This mixture is consolidated under suitable conditions in an extruder and, for example, extruded through a 1 mm sieve plate. If required, the extrudate strips thus obtained are rounded off in a spheronizer and then dried.

The dried extrudate is mixed with the nimodipine coprecipitate, NO-ASA and magnesium stearate and compressed in suitable tablet machines (11 mm diameter).

Example 20

Delayed Release Tablet

| | |
|---|---|
| NO-ASA | 30 mg |
| Nimodipine coprecipitate | 40 mg (10 mg nimodipine) |
| Vitamin A | 1 mg (3000 I.U.) |
| Thiamine nitrate | 10 mg |
| Riboflavin | 10 mg |
| Pyridoxine HCl | 5 mg |
| Cyanocobalamin | 5 µg |
| Nicotinamide | 50 mg |
| Ascorbic acid | 50 mg |
| D-α-tocopherol acetate | 15 mg |
| Dry extract of Gingko biloba leaves (50:1) standardized to 960 mg of gingko flavone glycosides and 240 mg of terpene lactones | 40 mg |
| HPMC 60 SH 50 | 200 mg |
| Magnesium stearate | 3 mg |
| Total weight | 474 mg |

Preparation

All constituents with the exception of the nimodipine coprecipitate, the NO-ASA and the magnesium stearate are moistened with a suitable amount of water in a customary mixer. This mixture is consolidated in an extruder under suitable conditions and, for example, extruded through a 1 mm sieve plate. If required, the extrudate strips thus obtained are rounded off in a spheronizer and then dried.

The dried extrudate is mixed with the nimodipine coprecipitate, NO-ASA and magnesium stearate and compressed in suitable tablet machines (11 mm diameter).

What is claimed is:

1. Combinations of at least one dihydropyridine compound of the formula (I),

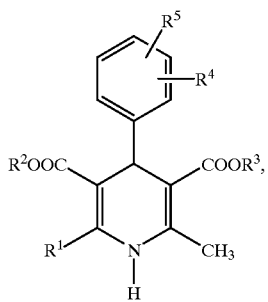

in which

R$^1$ represents cyano or alkyl having 1 to 4 C atoms, which is optionally substituted by hydroxyl, or the radical OCH$_2$CH$_2$NH$_2$, R$^2$ and R$^3$ are identical or different and in each case represent alkyl having 1 to 4 C atoms, which is optionally substituted by alkoxy having 1 to 4 C atoms or by an N-methylbenzyl radical, R$^4$ and R$^5$ are identical or different and in each case represent hydrogen, nitro, trifluoromethyl, chlorine or the radical OCHF$_2$ or together with, the phenyl ring represent the radical

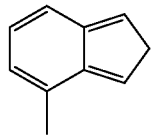

with at least one acetylsalicylic acid nitroesters of the formula (II)

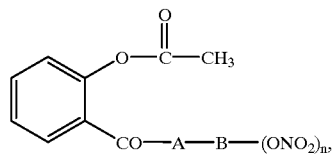

in which

A represents oxygen or NH,

B represents a straight-chain or branched alkylene radical having 2 to 7 C atoms, a cycloalkylene radical having 3 to 7 C atoms or an aralkylene radical having 7 to 12 C atoms and n represents a number from 1 to 5, and with at least one vitamin selected from the group consisting of the vitamins A, B, C, D, E and β-carotene and, optionally, with gingko extract as a further active compound component.

2. A compound according to claim 1, comprising combination components containing acetylsalicylic acid nitroesters of the formula (II) in which A and B have the meaning given in claim 1 and n represents a number from 1 to 3.

3. A compound according to claim 1 wherein the dihydropyridines are selected from the group consisting of nifedipine, amlodipine, nimodipine, nitrendipine ad nisoldipine.

4. A compound according to claim 1, comprising acetylsalicylic acid compounds of the formula (II), in which A represents oxygen, B represents an alkylene group having 2 to 6 carbon atoms and n represents a number from 1 to 3.

5. A pharmaceutical composition comprising a pharmaceutically effective amount of a compound according to claim 1 and a pharmaceutically acceptable auxiliary or excipient.

* * * * *